United States Patent [19]

Bringer et al.

[11] Patent Number: 4,742,006

[45] Date of Patent: May 3, 1988

[54] **FERMENTATION PROCESS FOR THE PRODUCTION OF FRUCTOSE FROM AQUEOUS MIXTURES OF FRUCTOSE AND GLUCOSE AND *ZYMOMONAS MOBILIS* MUTANTS WHICH CAN BE USED FOR SUCH FERMENTATION**

[75] Inventors: Stephanie Bringer; Hermann Sahm, both of Jülich, Fed. Rep. of Germany

[73] Assignee: Kernforschungsanlage Jülich Gesellschaft mit beschränkter Haftung, Jülich, Fed. Rep. of Germany

[21] Appl. No.: 795,422

[22] Filed: Nov. 6, 1985

[30] Foreign Application Priority Data

Aug. 13, 1985 [DE] Fed. Rep. of Germany ....... 3528933

[51] Int. Cl.$^4$ .................... C12P 19/02; C12N 15/00; C12N 1/20; C13L 3/00; C12R 1/01
[52] U.S. Cl. ................. 435/105; 435/172.1; 435/253; 435/274; 435/822
[58] Field of Search ............. 435/94, 105, 274, 172.1, 435/253

[56] References Cited

U.S. PATENT DOCUMENTS

| | | | |
|---|---|---|---|
| 4,356,262 | 10/1982 | Heady | 435/97 |
| 4,403,034 | 9/1983 | Rogers et al. | 435/161 |
| 4,413,058 | 11/1983 | Arcuri et al. | 435/161 |
| 4,443,543 | 4/1984 | Rogers et al. | 435/161 |

FOREIGN PATENT DOCUMENTS

2953084 6/1984 Australia .

OTHER PUBLICATIONS

Barrow et al., Applied Microbiology and Biotechnology (1984), vol. 20, pp. 225–232.

ATCC Catalogue of Bacteria, 16th edition, 1985, p. 220.
"Formation of Sorbitol by *Zymomonas mobilis*", Applied Microbiology and Biotechnology, 1980, 20, 118–123.
Abstract No. 39, "Induction, Isolation, and Characteristics of Fructose–Negative Mutants of *Zymomonas mobilis*", S. Bringer, M. Scollar and H. Sahm, Institut für Biotechnologie der Kernforschungsanlage Jülich GmbH, presented at 11th Int. Carbohydrate Sumposium, Vancouver, Canada, Aug. 22–28, 1982.
T. E. Barman, 1969, Enzyme Handbook I, p. 310.
"Levan Formation by *Zymomonas mobilis*", D. W. Ribbons, E. A. Dawes, D. A. Rees, 1962, Biochem. J. 82, p. 45.
"The Kinetics of Ethanol Production by *Zymomonas mobilis* on Fructose and Sucrose Media", K. J. Lee, et al., 1981, Biotechnol. Lett. 3, pp. 207–212.
"Sucrose Utilization by *Zymomonas mobilis:* Formation of a Levan", E. A. Dawes, D. W. Ribbons & D. A. Rees, Biochem. J. (1966) 98, pp. 804–812.
"The Biology of *Zymomonas*", J. Swings and J. DeLay, Bacteriological Reviews, Mar. 1977, vol. 41, No. 1, pp. 1–46.
"The Carbohydrates: Chemistry and Biochemistry", Second Edition, edited by Ward Pigman and Derek Horton, 1980 Academic Press, vol. 1B, p. 1445.
"The Carbohydrates: Chemistry and Biochemistry", Second Edition, edited by Ward Pigman & Derek Horton, 1980 Academic Press, vol. 1A, p. 91.

*Primary Examiner*—Lionel M. Shapiro
*Attorney, Agent, or Firm*—Nils H. Ljungman

[57] ABSTRACT

A method of producing fructose from aqueous glucose and fructose mixtures by fermenting in one step an aqueous mixture of fructose and glucose with a stable mutant of *Zymomonas mobilis*, and also producing the stable mutant of *Zymomonas mobilis*.

14 Claims, No Drawings

FERMENTATION PROCESS FOR THE PRODUCTION OF FRUCTOSE FROM AQUEOUS MIXTURES OF FRUCTOSE AND GLUCOSE AND ZYMOMONAS MOBILIS MUTANTS WHICH CAN BE USED FOR SUCH FERMENTATION

BACKGROUND OF THE INVENTION

1. Field of the Invention

The invention relates to a process for gaining or enrichment of fructose and, more particularly, to the fermentation of glucose accompanying fructose by a mutant of Zymomonas mobilis which does not decompose fructose.

The invention also relates to Zymomonas mobilis mutants which can be used for the purpose of producing fructose from glucose/fructose mixtures.

2. Description of the Prior Art

Because fructose is one and one-half times as sweet as sucrose, it is a valuable sweetener, which is used primarily for pharmaceutical purposes and for low-calorie foods. Glucose and fructose are both sugars which are included in the family of compounds comprising carbohydrates of which starches also form a part.

The customary processes for the extraction of fructose start with invert sugar or High Fructose Corn Syrup (HFCS), that is, mixtures of glucose and fructose. From this, the fructose is derived by separation processes such as crystallization, precipitation or chromatography, and sometimes with complexing, for example, with boric acid or conversion of the glucose into gluconic acid. These separation processes are relatively expensive because of the similarity of the two sugars and, therefore, attempts have already been made to develop enzymatic or microbial processes.

U.S. Pat. No. 4,356,262, which is incorporated herein by reference, describes a process for obtaining fructose syrup and ethanol from a sucrose solution. In this process, fructose polymers and ethanol are formed by Pullalaria pullulans and yeasts such as Saccharomyces bailii or cerevisiae by means of fructosyltransferase, and can then be hydrolyzed into fructose. But this process, which begins with sucrose, requires numerous complicated preparation and reaction steps. To get the special enzyme necessary for the transfructolysis, a special micro-organism must be cultivated in advance and prepared. The fermentation yeast, which must be added at the same time as the enzyme or added in a separate step, then converts the resulting glucose directly into ethanol. The technically very desirable fructose is obtained only as a polymer, and must subsequently be hydrolyzed in an additional step and under difficult conditions. Technically, such a complicated process seems far too expensive for obtaining fructose.

In Australian Patent Abstract No. AU-A 29 530/84, which is incorporated herein by reference, a process is described for the production of fructose and ethanol from sucrose, where the sucrose concentration must be greater than or equal to 30 percent by weight. By means of the bacterium Zymomonas mobilis, preferably after pre-treatment of the sucrose solution with an immobilized levan sucrase enzyme preparation (EC 2.4.1.10), there is a selective conversion of the glucose to ethanol within 1-2 days. However, this process also has significant disadvantages, in that the enzyme levan sucrase, according to EC 2.4.1.10, is in effect a fructosyltransferase, that is, the reaction products from sucrose are polyfructose (levan) and glucose. (T. E. Barman, 1969, Enzyme Handbook I, page 310, which is incorporated herein by reference.) It is also known that Zymomonas also produces levan from sucrose (D. W. Ribbons, 1962, Biochem. J. 82, 45 p; E. A. Dawes et al., 1966, Biochem. J. 98, 804; K. J. Lee, 1981, Biotechnol. Lett. 3 207, incorporated herein by reference.) The process according to the Australian Patent AU-A 29 530/84 also leads to the formation of levan, and therefore to significant slime formation. Naturally, the formation of levan also causes losses of monomer fructose. In addition, known strains of Zymomonas mobilis also convert fructose to ethanol, which also necessarily decreases the fructose yield in the above process. (Swings and DeLey, 1977, Bacteriol. Rev. 41, 1, incorporated herein by reference.)

A presentation was made at the 11th International Carbohydrate Symposium in Vancouver (S. Bringer, M. Scollar, H. Sahm, 1982, Abstract No. 39, incorporated herein by reference) concerning tests for the derivation of fructose-negative mutants of Zymomonas mobilis. The mutants indicated for this purpose, however, turned out to be unsuitable for practical use in the enrichment of fructose from mixtures of fructose and glucose, since the mutants were too unstable and unexpectedly lost their selectivity again even after a short time.

According to the known and sometimes very expensive methods, therefore, large proportions of undesirable by-products are produced, or the initially suitable microorganisms are stable only for a short time.

OBJECTS OF THE INVENTION

One object of the invention is therefore to provide a processfor the production of fructose, which reliably produces high fructose yields even over long periods of time.

Another object of the invention is to provide a mutant of Zymomonas mobilis which reliably produces high fructose yields even over long periods of time.

Yet another object of the invention is to provide a process for the production of sorbitol, which reliably produces high sorbitol yields even over long periods of time.

SUMMARY OF THE INVENTION

The method developed for the purpose of producing fructose is characterized by the fact that the fermentation is conducted by means of a mutant of Zymomonas mobilis stable in continuous culture for at least 10 days, preferably 100 days. The stable Zymomonas mobilis mutant was produced by continuous culturing of a Zymomonas mobilis mutant for at least 10 days.

Surprisingly, it was found that high fructose yields can be obtained from aqueous mixtures containing glucose and fructose, if the fermentation of glucose to ethanol is performed with stable fructose-negative mutants of Zymomonas mobilis, which retain the fructose-negativity unchanged for at least 10 days, preferably at least 100 days. In addition to the simplicity of execution of the one-step process, it is particularly advantageous that no fructose polymers are formed, which form slime and make the process more difficult.

Preferably, this fructose extraction or enrichment is done from aqueous mixtures, which contain at least 1%, preferably 4% to 13%, and specifically 7.5% to 10% of each glucose and fructose, whereby the process can be conducted either in batches, fed batches or continuously.

The isolation of fructose from the reaction mixture can be performed using known methods, for example, by chromatography, or fractionated precipitation. Examples of these methods are found in "The Carbohydrates, Chemistry and Biochemistry", 2nd Edition, edited by W. Pigman and D. Horton, Academic Press, New York and London, Volume 1A, page 91, and Volume 1B, page 1445, which is incorporated herein by reference in its entirety.

The invention also comprises special new stable mutants of *Zymomonas mobilis*, which produce ethanol and $CO_2$ in glucose/fructose mixtures only from glucose, but not from fructose, and which retain this characteristic for at least 10 days.

It specifically comprises the mutants with Registration Number DSM 3126 registered with the Deutsche Sammlung von Mikroorganismen, Grisebachstrasse 8, D-3400 Göttingen, Federal Republic of Germany.

The percentages indicated below, unless noted otherwise, are always percentages by weight.

The use of low sugar concentrations (1% to 4% each fructose and glucose) has the advantage that the glucose fermentation takes place quickly and the fructose remains almost entirely behind. If, on the other hand, highly concentrated sugar solutions are used (for example, more than 20% each fructose and glucose), the reaction periods are several times longer and the fructose yield drops. According to the method proposed by the invention, especially with higher concentrations of the initial solution, sorbitol is increasingly formed as the only by-product originating from the fructose. Sorbitol is a reduction product of fructose, and is also of great importance in the foods industry as a replacement for sugar, specifically in dietetic products. Therefore, substrate concentrations of 7.5% to 10% each of glucose and fructose are particularly preferred for yielding product solutions containing primarily fructose and ethanol.

To decrease the reduction of fructose to sorbitol by *Zymomonas mobilis*, which takes place to a significant extent only in the presence of high glucose concentrations, the fructose yield of the process described by the invention can be further increased by the following fermentation methods, in which the glucose concentration is kept low. Fed batch and continuous systems are particularly well-suited for this purpose. Thus, high glucose concentrations are prevented in fed batch fermentations, in which successively, after the fermentation of the initial substrate solution, this initial concentration is re-established by the addition of concentrated fructose/glucose solution (for example, each 40%). By means of the mutants according to the invention, for example, with a redosing of substrate solution 10 times into a culture with an initial concentration of 2% of each fructose and glucose, product solutions are obtained which contain 12% to 15% fructose and 7.5% to 10% ethanol. Continuous fermentations, which are conducted under glucose limitation and with substrate concentrations of 5% to 13% each, preferably 10% to 12% each glucose and fructose, lead to similarly high fructose yields. These two methods, fed batch and continuous fermentation, can only be successfully used with the mutants according to the invention for gaining fructose from glucose/fructose mixtures, since the naturally occurring strains of *Zymomonas mobilis* ferment fructose almost totally to ethanol, if the glucose concentrations present are low.

The induction of the mutants according to the invention in naturally occurring strains of *Zymomonas mobilis* can be done by irradiation of the cells with ultraviolet light, or preferably by chemical mutagenesis with non-alkylating agents such as nitrite, bisulfite, hydroxylamine, or with alkylating agents such as alkylalkane sulfonate (for example, ethylmethanesulfonate, ethylethanesulfonate, diethylsulfate) and N-nitroso compounds (for example, dialkyl nitroso amine, N-nitroso ureas, N-alkyl-N'-nitro-N-nitroso-guanidine). The alkylating agent N-methyl-N'-nitro-N-nitroso-guanidine is particularly preferred.

Suitable media for the cultivation of the mutants according to the invention include those which contain the following components:

$KH_2PO_4$: 0.5–1.0 grams per liter water (g/l $H_2O$);
$(NH_4)_2SO_4$: 0.5–1.0 grams per liter water;
$MgSO_4 \times 7H_2O$: 0.5–0.75 grams per liter water;
yeast extract: 5–10 grams per liter water; and
fermentable sugar (glucose): 10–130 grams per liter water.

The pH value of the medium should be between 4 and 7 at the beginning and during the fermentation, and the temperature between 25° C. and 37° C., and preferably between 28° C. and 32° C.

Further characteristics of the invention are indicated in the following description of the invention and examples.

(1) Induction and Selection of Fructose-Negative Stable Mutants

A suspension of cells of the naturally occurring strain, *Zymomonas mobilis* having Registration Number ATCC 29191, available from the American Type Culture Collection, 12301 Parklawn Drive, Rockville, Md. 20852, U.S.A., was prepared having a cell density of $2.8 \times 10^8$ live cells/ml, which cell density corresponds to an optical density ($OD_{550\ nm}$) of 7.0. The cells suspended in a 0.1M potassium phosphate buffer having a pH of 6.0, and were treated with N-methyl-N'-nitro-N-nitroso-guanidine (NTG) ($1.9 \times 10^{-4}$M final concentration). After 15 minutes of incubation at room temperature, the cells were washed twice with 0.9% NaCl solution. To accentuate the mutation, a 20-hour incubation followed in a liquid medium. The liquid medium had the following composition:

$KH_2PO_4$: 1.0 grams per liter water (g/l $H_2O$);
$(NH_4)_2SO_4$: 1.0 grams per liter water;
$MgSO_4 \times 7H_2O$: 0.5 grams per liter water;
yeast extract: 5 grams per liter water; and
the liquid medium had a pH=5.0

The liquid medium had 2% glucose therein and the incubation was carried out at 30° C. There was a subsequent incubation in a liquid medium with 2% fructose+0.3 mg/ml ampicillin for mutant enrichment. These accentuation and enrichment phases were repeated three times. Fructose-negative mutants were identified and isolated by replication on agar plates containing glucose or fructose (Liquid medium+2% agar). A fructose-negative mutant is one which cannot grow on fructose as a single carbon and energy source. Fructose negativity is discussed in "Fructose Negative and Glycerol Negative Derivatives of Glucose 6 Phosphate Dehydrogenase Deficient Mutants of Pseudomonas-Aeruginosa", authored by P. V. Phibbs, Jr., S. M. McCowen, and T. W. Feary, *Abstract of the Annual Meeting of the American Society of Microbiology*, (79), 1979 16, and also in "Isolation and Characterization of Mutants of Hydrogenomonas-Eutropha Strain H-16

Defective in Catabolism Part 1 Fructose Negative Mutants", authored by B. Bowien and H. G. Schlegel, *Arch Mikrobiol.*, 87 (3), 1972 (Recd. 1973) 203-219, both of which are incorporated herein by reference.

The stability of the fructose-negative mutants was verified by spreading undiluted culture specimens on agar plates containing fructose (fluid medium+2% agar). Cultures of the Mutant DSM 3126 remained stable in the fluid culture during and after a period of 6 months, with reinjection periods of 2 to 7 days. The fructose-negativity of these mutants also remained unchanged during growth in continuous culture for 10 days.

(2) Fructose Extraction

EXAMPLE 1

A medium comprising 18.2 g/l fructose and 20.6 g/l glucose, dissolved in the fluid medium described in Section 1), was inoculated in a pH and temperature-controlled fermenter with 10% by volume of a pre-culture of the *Zymomonas mobilis* DSM 3126 mutant grown on the same medium. From the time of the initial inoculation until the end of the fermentation, the pH value was kept at 5.0 and the temperature at 30° C. The results are indicated in Table 1.

EXAMPLES 2 AND 3

The fermentations were conducted as in Example 1, but with a variation of the initial sugar concentrations. The results are shown in Table 1.

It is apparent that glucose is relatively rapidly and practically completely decomposed in a relatively dilute sugar solution, while a considerable conversion of fructose to sorbitol occurs only at higher fructose concentrations and longer fermentation times.

The invention as described hereinabove in the context of the preferred embodiment is not to be taken as limited to all of the provided details thereof, since modifications and variations thereof may be made without departing from the spirit and scope of the invention.

TABLE 1

|  | Example 1 | Example 2 | Example 3 |
|---|---|---|---|
| Initial concentrations: |  |  |  |
| Fructose (g/l) | 18.2 | 48.3 | 98.5 |
| Glucose (g/l) | 20.6 | 49.9 | 100.2 |
| Final concentrations: |  |  |  |
| Fructose (g/l) | 15.9 | 33.9 | 72.7 |
| Glucose (g/l) | 0.0 | 0.0 | 0.6 |
| Ethanol (g/l) | 8.2 | 22.0 | 42.5 |
| Sorbitol (g/l) | 2.1 | 10.6 | 24.5 |
| Fermentation period (hours) | 8.0 | 11.0 | 30.0 |
| Fructose enrichment: |  |  |  |
| percent of Fructose to total sugar | 100.0 | 100.0 | 99.0 |

10 grams per liter = one percent by weight

What is claimed is:

1. Process for gaining or enrichment of fructose from glucose/fructose mixtures by converting glucose, said process comprising the steps of:
    introducing into an aqueous mixture of glucose and fructose a stable mutant of *Zymomonas mobilis;* and
    fermenting said aqueous mixture of glucose and fructose by the action of said stable mutant of *Zymomonas mobilis;*
    said *Zymomonas mobilis* converting at least a portion of said glucose in said aqueous mixture by said fermentation into ethanol and $CO_2$;
    said stable *Zymomonas mobilis* mutant being substantially incapable of converting fructose to ethanol and carbon dioxide; and
    said stable *Zymomonas mobilis* mutant having been produced by continuous culturing of a *Zymomonas mobilis* mutant for at least about 10 days.

2. The process according to claim 1, wherein said continuous culturing of said *Zymomonas mobilis* mutant is continued for about 100 days.

3. The process according to claim 1, wherein said fermenting performed by the *Zymomonas mobilis* mutant is the strain of *Zymomonas mobilis* which has a registration number of DSM 3126.

4. The process according to claim 1, wherein said aqueous mixture containing fructose and glucose contains at least one percent glucose and at least one percent fructose.

5. The process according to claim 1, wherein said aqueous mixture containing fructose and glucose contains four percent to thirteen percent of glucose and four percent and thirteen percent of fructose.

6. The process according to claim 1, wherein said aqueous mixture containing fructose and glucose contains 7.5 percent to ten percent of glucose and 7.5 percent and ten percent of fructose.

7. The process according to claim 1, wherein said fermenting is carried on continuously.

8. Process for producing sorbitol from an aqueous glucose and fructose mixture, said process comprising the steps of:
    introducing into a mixture of glucose and fructose and water a stable mutant of *Zymomonas mobilis;* and
    fermenting said aqueous mixture;
    said *Zymomonas mobilis* converting a portion of said fructose in said mixture by said fermentation into sorbitol;
    said stable *Zymomonas mobilis* mutant being substantially incapable of converting fructose to ethanol and carbon dioxide;
    said stable *Zymomonas mobilis* mutant having been produced by continuous culturing of a *Zymomonas mobilis* mutant for at least about 10 days.

9. Process for converting a glucose and fructose mixture to fructose and sorbitol, said process comprising the steps of:
    introducing into an aqueous mixture of glucose and fructose a stable mutant of *Zymomonas mobilis;*
    fermenting said aqueous mixture of glucose and fructose;
    said *Zymomonas mobilis* converting at least a portion of said glucose in said aqueous mixture to ethanol and $CO_2$ by said fermentation and a portion of said fructose into sorbitol;
    said stable *Zymomonas mobilis* mutant being substantially incapable of converting fructose to ethanol and carbon dioxide; and
    said stable *Zymomonas mobilis* mutant having been produced by continuous culturing of a *Zymomonas mobilis* mutant for at least about 10 days.

10. The process according to claim 9 including recovering said fructose and recovering said sorbitol.

11. A mutant of *Zymomonas mobilis* which selectively decomposes glucose in mixtures of glucose and fructose to produce or enrich fructose during fermentation, said mutant of *Zymomonas mobilis* produced by the steps of:
    mutating the naturally occurring strain of *Zymomonas mobilis;* isolating fructose-negative mutants of said mutation; and selecting stable mutants of said fructose-negative mutants by continuously culturing said fructose-negative mutants for at least about ten days.

12. The mutant of *Zymomonas mobilis* according to claim 11 wherein said mutations are produced by at least one mutagen selected from the group consisting essentially of physical mutagens and chemical mutagens.

13. The mutant of *Zymomonas mobilis* according to claim 12 wherein said mutations are produced by treatment of said *Zymomonas mobilis* with N-methyl-N'-nitro-N-nitroso-guanidine.

14. The mutant of *Zymomonas mobilis* according to claim 13 wherein said mutants comprise a mutant which has a Registration Number of DSM 3126.

* * * * *